United States Patent [19]

Merger et al.

[11] Patent Number: 4,873,362
[45] Date of Patent: Oct. 10, 1989

[54] PREPARATION OF 2-SUBSTITUTED 4-ACYLOXY-2-BUTENALS

[75] Inventors: Franz Merger, Frankenthal; Rolf Fischer, Heidelberg; Hans Horler, Darmstadt, all of Fed. Rep. of Germany

[73] Assignee: BASF Aktiengesellschaft, Ludwigshafen, Fed. Rep. of Germany

[21] Appl. No.: 115,891

[22] Filed: Nov. 2, 1987

[30] Foreign Application Priority Data

Nov. 20, 1986 [DE] Fed. Rep. of Germany ....... 3639562

[51] Int. Cl.$^4$ .............................................. C07C 67/00
[52] U.S. Cl. ................................... 560/238; 560/177; 546/341; 260/404.5
[58] Field of Search .............................. 560/238, 177; 260/405.5; 546/341

[56] References Cited

U.S. PATENT DOCUMENTS 3,840,589 10/1974 Himmele et al. .................. 560/238

FOREIGN PATENT DOCUMENTS 0010656 5/1980 European Pat. Off. .
2124608 9/1972 France .
7900485 7/1979 World Int. Prop. O. .

*Primary Examiner*—Werren B. Lone
*Attorney, Agent, or Firm*—Oblon, Spivak, McClelland, Maier & Neustadt

[57] ABSTRACT

2-Substituted 4-acyloxy-2-butenals of the general formula I

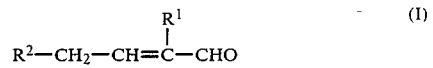

where $R^1$ is alkyl of 1 to 12 carbon atoms which may be substituted by cycloalphatic, aromatic or heterocyclic radicals, by alkenyl or alkynyl or by hydroxyl, ether, thioether, acetoxy acyl, alkylamino, carboxyl or carbalkoxy, and $R^2$ is acyloxy, are prepared by reacting a monosubstituted acetaldehyde of the general formula II

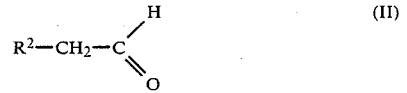

where $R^2$ has the abovementioned meaning, with an aldehyde of the general formula III .

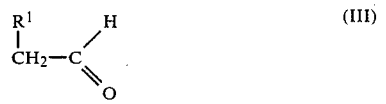

where $R^1$ has the abovementioned meaning, in the presence of a linear or cyclic secondary amine and of an organic acid at from 20° to 100° C.

12 Claims, No Drawings

PREPARATION OF 2-SUBSTITUTED 4-ACYLOXY-2-BUTENALS

The present invention relates to a process for preparing a 2-substituted 4-acyloxy-2-butenal by reacting an acyloxyacetaldehyde with an aldehyde having 2α hydrogens.

4-Acyloxy-2-alkyl-2-butenals are useful building blocks for the preparation of terpenes having biological and pharmacological activity, such as vitamin A. Accordingly, a number of processes have been described for their preparation. For instance, (E)-4-acetoxy-2-methyl-2-butenal can be prepared from butynediol by first partially hydrogenating butynediol to 2-butene-1,4-diol, then rearranging to 1-butene-3,4-diol and finally acetylating to 1-butene-3,4-diol diacetate which, by hydroformylation and elimination of acetic acid, gives (E)-4-acetoxy-2-methyl-2-butenal (cf. DE 1,941,632).

A further existing method of preparation comprises subjecting methylglyoxal dimethyl acetal to ethynylation and subsequent partial hydrogenation to give 2-hydroxy-2-methyl-3-butenal dimethyl acetal, acetylating, and rearranging the resulting 2-acetoxy-2-methyl-3-butenal dimethyl acetal in the presence of copper catalysts to 4-acetoxy-2-methyl-2-methyl-2-butenal dimethyl acetal, which can then be selectively hydrolyzed to (E)-4-acetoxy-2-methyl-2-butenal (cf. DE 1,297,597).

The disadvantage with these pathways is the large number of reaction steps required to prepare the desired 4-acyloxy-2-alkyl-2-butenals.

It is an object of the invention to develop a process whereby the desired 4-acyloxy-2-alkyl-2-butenals can be prepared in a substantially simpler manner.

We have found that this object is achieved with a process for preparing a 2-substituted 4-acyloxy-2-butenal of the general formula I

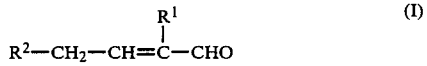

where $R^1$ is alkyl of 1 to 12 carbon atoms, preferably 1 to 4 carbon atoms, which may be substituted by cycloaliphatic, aromatic or heterocyclic radicals, by alkenyl or alkynyl or by hydroxyl, ether, thioether, acyl, alkylamino, carboxyl or carbalkoxy, and $R^2$ is acyloxy of 1 to 12 carbon atoms, preferably 1 to 4 carbon atoms, which comprises reacting an acyloxyacetaldehyde of the general formula II

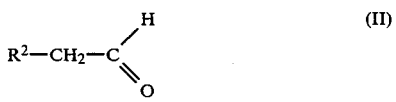

where $R^2$ has the abovementioned meaning, with an aldehyde of the general formula III

where $R^1$ has the abovementioned meaning, in the presence of a secondary amine and of an organic acid at from 20° to 100° C., preferably 30° to 80° C.

The advantageous result of the process according to the invention, which makes it possible to react acyloxyacetaldehydes of the formula II in only one reaction step with the aldehydes of formula III to give substantially the desired 2-substituted 4-acyloxy-2-butenals, was not foreseeable from the prior art. It is surprising that, under the reaction conditions according to the invention, this reaction of two different aldehydes which each have two reactive hydrogen atoms in the α-position relative to the formyl group preferentially produces the desired 2-substituted 4-acyloxy-2-butenals and not a large number of condensation products which could have been expected. Of the possible condensation products of the formulae

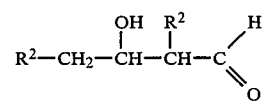

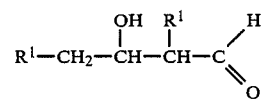

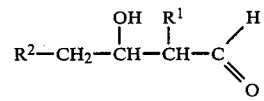

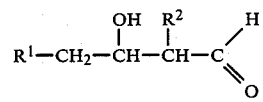

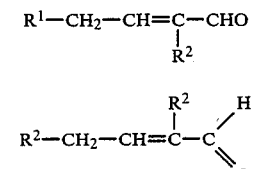

and

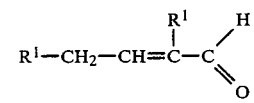

only the lastmentioned autocondensation product of the aldehyde of the formula III occurs as a by-product in a somewhat greater amount.

Usable acyloxyacetaldehydes of the formula II are for example: acetoxyacetaldehyde, propionyloxyacetaldehyde, butyryloxyacetaldehyde, isobutyryloxyacetaldehyde and pivaloyloxyacetaldehyde. Preference is given to acetaldehydes of the formula II in which $R^2$ is acyloxy of preferably 1 to 4 carbon atoms. Reaction with acetoxyacetaldehyde is particularly important.

In the aldehydes of the formula III, $R^1$ is for example straight-chain or branched alkyl of 1 to 12, preferably 1 to 8, carbon atoms, in particular 1 to 4 carbon atoms, which may contain cycloaliphatic, aromatic or heterocyclic radicals, such as phenyl, pyridyl, or alkenyl, alkynyl, hydroxyl, alkoxy, thioether, acetoxy, alkylamino, carboxyl or carbalkoxy.

Specific examples of aldehydes of the formula III are: propanal, butanal, pentanal, 3-pentenal, 4-pentenal, 3-methylbutanal, 3-phenylpropanal, 3-phenylbutanal, 3-anisylpropanal, 3-anisylbutanal, 3-pyridylpropanal, 4-hydroxybutanal, 4-acetoxybutanal, 5-formylvaleric acid, 5-formylvaleric esters, 4-dimethylaminobutanal, 3-methylthiopropanal, 4-methylthiobutanal, 3,6-dioxaheptanal, 3,5-dimethyloct-5-en-1al, 4-oxapentanal and 4,7-dioxaoctanal. Preferred aldehydes of the formula III are those in which $R^1$ is alkyl of preferably 1 to 4 carbon atoms. The reaction with propanal is of particular importance.

The process according to the invention is carried out in the presence of a catalyst system comprising a linear or cyclic secondary amine and an organic acid, in particular a carboxylic acid. Examples of suitable linear secondary amines are dialkylamines, such as dimethylamine, diethylamine, diisopropylamine, di(iso)butylamine, methylethylamine, methylbutylamine, ethylbutylamine and methylhydroxyethylamine. Usable cyclic amines are for example pyrrolidine, piperidine and morpholine.

The organic acid used can be a monobasic or even a dibasic or higher basic acid. Particularly suitable acids are mono- and dicarboxylic acids, such as acetic acid, propionic acid, (iso)butyric acid, (iso)valeric acid, 2-methylbutyric acid, hexanoic acid, methylpentanoic acid, ethylhexanoic acid, isononanoic acid, methoxyacetic acid, pivalic acid, methoxypivalic acid, oxalic acid, succinic acid, glutaric acid, adipic acid, hydroxybutyric acid, malic acid and hydroxypivalic acid. If an aldehydric acid is used, such as 5-formylvaleric acid, the use of an additional carboxylic acid is not necessary.

Cataysts of this type are described for example in EP-B-58,927. With these catalysts it is not necessary, although advantageous, to use the amine and the acid in equivalent amounts. However, it is also possible to use from 1 to 1.5 equivalents of acid per equivalent of amine. The amount of catalyst used for the reaction is likewise variable within wide limits. The amount of catalyst used is advantageously from 1 to 150, preferably from 5 to 100, in particular from 20 to 100, mol %, based on the starting material of formula II. If, to obtain a rapid reaction under mild conditions, a more than insignificant, catalytic amount of catalyst is used (ie. for example more than 5 mol %, based on II), the catalyst will be recovered after the product has been separated off, for example by phase separation, extraction or distillation, and used again, so that the overall result is a low consumption.

The condensation according to the invention proceeds particularly advantageously if additionally carried out in the presence of from about 5 to 70, preferably from about 10 to 50, % by weight of water in the reaction mixture. The presence of water facilitates in particular the working up of the reaction mixture, since the catalyst is easier to separate off with water.

The reaction is generaly carried out at from about 20° to 100° C., preferably from about 30° to 80° C. In general, the reaction is carried out under atmospheric pressure; but in principle it is also possible to work under reduced or superatmospheric pressure. The process can be carried out batchwise or, alternatively, continuously.

The starting materials are used in molar ratios of aldehyde of the formula III: acetaldehyde of the formula II of from 1:1 to 10:1, preferably from 1.4 to 7.5:1, in particular from 1.5 to 6:1.

The processis advantageously carried out by slowly introducing the starting aldehydes with stirring simultaneously or even dissolved in each other into the hot and facultatively water-containing catalyst mixture at reaction temperature while maintaining the reaction temperature by cooling, and then keeping the reaction mixture, advantageously with stirring, at the reaction temperature for a further period. The length of this period depends on the nature of the starting compounds and on the reaction temperature, ranging in general from 5 to 240 minutes.

The process according to the invention is thus distinguished by technical simplicity. Many of the starting compounds are available at commercially favorable cost. For instance, the acetoxyaldehyde required for preparing the vitamin A intermediate 4-acetoxy-2-methyl-2-butenal is obtainable in a relatively simple manner from ethylene oxide and acetic anhydride by oxidation of ethylene glycol monoacetate. Propionaldehyde is a commercial compound.

The Examples which follow illustrate the process according to the invention.

EXAMPLES 1 TO 5

To a mixture of 120 g (2 mol) of acetic acid and 225 g of a 40% strength by weight aqueous solution of dimethylamine ($\hat{=}2$ mol of dimethylamine and 66% by weight based on starting II, or in Examples 1 to 3 17.3%, based on the total reaction mixture, of water) was added with stirring and cooling at the temperature (T) revealed in Table 1 and within the time (Z) revealed in Table 1 a solution of the amount of acetoxyaldehyde revealed in Table 1 in the amount of propionaldehyde revealed in Table 1. The reaction mixture was then maintained with stirring at the reaction temperature for the period (NZ) revealed in Table 1. After the reaction mixture had cooled down to room temperature, the bottom phase of aqueous catalyst solution was separated off, and the organic phase subjected to fractional distillation. The stated yields are based on starting acetoxyacetaldehyde.

TABLE 1

| Example | T [°C.] | Z [min] | Acetoxy-acetaldehyde [g (mol)] | Propion-aldehyde [g (mol)] | NZ [min] | (E)-4-Acetoxy-2-methyl-2-butenal Yield [g (% of theory)] | b.p. [°C./mbar] | 2-Methyl-2-pentenal Yield [g] |
|---|---|---|---|---|---|---|---|---|
| 1 | 50 | 30 | 204 (2) | 232 (4) | 30 | 153 (54) | 60–67/1 | 139 |
| 2 | 80 | 5 | 204 (2) | 232 (4) | 10 | 176 (62) | 60–64/1 | 130 |
| 3 | 30 | 15 | 204 (2) | 232 (4) | 240 | 125 (44) | 58–67/1 | 148 |
| 4 | 50 | 15 | 204 (2) | 128 (2.2) | 30 | 119 (42) | 62–67/1 | 61 |
| 5 | 50 | 30 | 204 (2) | 580 (10) | 30 | 179 (63) | 60–75/2 | 421 |

EXAMPLE 6

To a mixture of 225 g of a 40% strength by weight aqueous solution of dimethylamine and 120 g of acetic acid was added with stirring and cooling, in the course of 15 min, a solution of 204 g of acetoxyacetaldehyde in 288 g (4 mol) of n-butyraldehyde, and the reaction mixture was subsequently stirred at 50° C. for 30 min. The reaction solutions were cooled down and the aqueous catalyst solution separated off to give, by fractional distillation, 169 g of 4-acetoxy-2-ethyl-2-butenal (b.p.=83°–93° C./6 mbar), corresponding to a yield of 54% of theory, based on acetoxyacetaldehyde, and 181 g of 2-ethyl-2-hexanal (b.p.=38°–70° C./20–60 mbar).

We claim:

1. A process for preparing a 2-substituted 4-acyloxy-2-butenal of formula I:

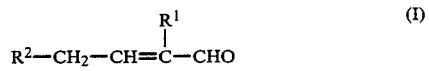

where $R^1$ is alkyl of 1 to 12 carbon atoms which may be substituted by cycloaliphatic, phenyl, anisyl, or heterocyclic radicals, by alkenyl or alkynyl or by hydroxyl, ether, thioether, acetoxy acyl, acetoxy alkylamino, carboxyl or carbalkoxy, and $R^2$ is acyloxy of 1 to 12 carbon atoms, which comprises:

reacting an acyloxyacetaldehyde of formula II:

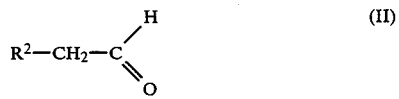

where $R^2$ has the abovementioned meaning, with an aldehyde of formula III:

where $R^1$ has the abovementioned meaning, in the presence of a linear or cyclic secondary amine and of a mono- or dicarboxylic acid at from 20° to 100° C.

2. A process as claimed in claim 1, wherein the aldehydes of the formulae II and III are reacted at from 30° to 80° C.

3. A process as claimed in claim 1, wherein the reaction is carried out in the presence of a mono- or dicarboxylic acid of 1 to 10 carbon atoms.

4. A process as claimed in claim 1, wherein the monosubstituted acetaldehyde of the general formula II is acetoxyacetaldehyde.

5. A process as claimed in claim 1, wherein the aldehyde of the formula III is propanal.

6. A process as claimed in claim 1, wherein the reaction is additionally carried out in the presence of water.

7. The process as claimed in claim 3, wherein said carboxylic acid is acetic acid, propionic acid, (iso)-butyric acid, (iso)valeric acid, 2-methylbutyric acid, hexanoic acid, methylpentanoic acid, ethylhexanoic acid, isononanoic acid, methoxyacetic acid, pivalic acid, methoxypivalic acid, oxalic acid, succinic acid, glutaric acid, adipic acid, hydroxybutyric acid, malic acid or hydroxypivalic acid.

8. The process as claimed in claim 1, wherein the mole ratio of aldehyde of formula (III) to aldehyde of formula (II) ranges from 1:1 to 10:1.

9. The process claimed in claim 8, wherein said mole ratio ranges from 1.4 to 7.5:1.

10. The process as claimed in claim 1, wherein said aldehyde of formula II is a member selected from the group consisting of acetoxyacetaldehyde, propionyloxyacetaldehyde, butyryloxyacetaldehyde, isobutyryloxyacetaldehyde and pivaloyloxyacetaldehyde.

11. The process as claimed in claim 1, wherein said aldehyde of formula III is a member selected from the group consisting of propanal, butanal, pentanal, 3-pentenal, 4-pentenal, 3-methylbutanal, 3-phenylpropanal, 3-phenylbutanal, 3-anisylpropanal, 3-anisylbutanal, 3-pyridylpropanal, 4-hydroxybutanal, 4-acetoxybutanal, 5-formylvaleric acid, 5-formylvaleric esters, 4-dimethylaminobutanal, 3-methylthiopropanal, 4-methylthiobutanal, 3,6-dioxaheptanal, 3,5-dimethyloct-5-en-1al, 4-oxapentanal and 4,7-dioxaoctanal.

12. The process as claimed in claim 1, wherein said amine catalyst is dimethylamine, diethylamine, diisopropylamine, di(iso)butylamine, methylethylamine, methylbutylamine, ethylbutylamine, methylhydroxyethylamine, pyrrolidine, piperidine or morpholine.

* * * * *